United States Patent [19]

Schouteeten et al.

[11] Patent Number: 4,504,678

[45] Date of Patent: Mar. 12, 1985

[54] PURE CRYSTALLINE RACEMIC SODIUM PARAHYDROXYMANDELATE, PROCESS FOR ITS PREPARATION AND USES THEREOF

[75] Inventors: Alain Schouteeten, Ezanville; Yani Christidis, Paris, both of France

[73] Assignee: Societe Francaise Hoechst, Puteaux, France

[21] Appl. No.: 455,143

[22] Filed: Jan. 3, 1983

Related U.S. Application Data

[62] Division of Ser. No. 284,835, Jul. 20, 1981.

[51] Int. Cl.$^3$ .............................................. C07C 59/50
[52] U.S. Cl. ................................................... 562/470
[58] Field of Search ........................................ 562/470

[56] References Cited

U.S. PATENT DOCUMENTS 4,198,523   4/1980   Copeland ............................ 562/470
4,368,334   1/1983   Dales .................................. 562/470

*Primary Examiner*—Paul J. Killos
*Attorney, Agent, or Firm*—Karl W. Flocks; Sheridan Neimark

[57] ABSTRACT

Pure crystalline racemic sodium parahydroxymandelate free from any ions of chloride, acetate, formate and sulfate group, is manufactured by condensing in water, in the presence of sodium hydroxide at a temperature between 30° and 100° C., glyoxylic acid or sodium glyoxylate with an excess of phenol, concentrating it hot, until the start of crystallization of the solution thus obtained after neutralization and removal of the unconverted phenol either by steam distillation, or by extraction with a water-immiscible organic solvent. The resulting suspension obtained is cooled, drained after some hours of standing at a temperature close to 5° C., and the resulting precipitate recovered by washing it with iced water followed by drying to constant weight. The product is useful for the manufacture of crystalline sodium paraformylphenolate.

4 Claims, No Drawings

PURE CRYSTALLINE RACEMIC SODIUM PARAHYDROXYMANDELATE, PROCESS FOR ITS PREPARATION AND USES THEREOF

This is a division of application Ser. No. 284,835 filed July 20, 1981.

BACKGROUND OF THE INVENTION

1. Field of the Invention

The present invention relates to pure crystalline racemic sodium parahydroxymandelate, the process for its preparation and its uses. It relates more particularly, by way of novel industrial product, to anhydrous crystalline racemic sodium parahydroxymandelate or racemic sodium parahydroxymandelate crystallized with one molecule of water free from any ions of chloride, acetate, formate, sulfate group and the like.

2. Description of the Prior Art

Certain salts of racemic parahydroxymandelic acid are described in the literature. Calcium parahydroxymandelate crystallized with 5.5 molecules of water and cinchonine parahydroxymandelate were isolated by A. ELLINGER et al., Z. Physiol. Chem., 65, 402–13, 1910. Intermediately, in the course of certain preparations of racemic parahydroxymandelic acid, either sodium parahydroxymandelate, or disodium 4-oxidomandelate have sometimes been obtained or used in aqueous sodium solution as, for example, in the alkaline hydrolysis of 4-dibenzoyloxy, α phenylacetamide according to J. ALOY et al., Bull. Soc. chim. France, 4, 11, 389–93 (1912) or of parahydroxyphenyltrichloromethylcarbinol according to H. HAAKH et al., Austrian Patent No. AT 141 159 or of ethyl parahydroxymandelate according to K. LANDENBURG et al., J. Amer. Chem. Soc. 58, 1292–94 (1936) or in the condensation of glyoxylic acid with phenol according to French Patent Application No. 78 31.123 of Nov. 3, 1978.

More recently solid monohydrate sodium parahydroxymandelate containing sodium chloride (about 10% by weight) has been isolated from its aqueous preparing solution from glyoxylic acid and phenol with salting by sodium chloride (see Belgium patent 867.287, Chemical Abstracts, 1979, 90, 870 67 g).

Moreover referring to U.S. Pat. No. 4,154,757, anhydrous sodium parahydroxymandelate having a purity of 99% only and containing 1% by weight of sodium chloride, is obtained from the monohydrate form by azeotropic removal of the water using toluene or xylene as azeotroping solvent.

However, insofar as is known, pure crystallized racemic sodium parahydroxymandelate (i.e not containing other anions such as chloride, acetate, formate, or sulfate) in anhydrous form or with one molecule of water has never been either isolated or described. Such a product free of chloride ions is suitable for preparing parahydroxybenzaldehyde by degradative oxidizing decarboxylation in a stainless steel reactor.

GENERAL DESCRIPTION OF THE INVENTION

According to the invention, crystalline racemic sodium parahydroxymandelate can be prepared, by condensing in water of glyoxylic acid or of sodium glyoxylate with an excess of phenol, desirably to 2 to 3 mols of phenol per mol of glyoxylic acid, in the presence of sodium hydroxide, desirably an amount of 2 to 3 mols per mol of glyoxylic acid, at a temperature between 30° and 100° C., desirably between 70° and 85° C., the start of crystallization of the solution thus obtained after neutralization with and acid such as acetic acid and removal of the unconverted phenol either by steam distillation or by extraction with a water-immiscible organic solvent, cooling the resulting suspension obtained, draining after some hours of standing at a temperature close to 5° C., recovering the resulting precipitate and washing it with iced water followed by drying at 40° C. to constant weight. Pure racemic sodium parahydroxymandelate crystallized with one molecule of water is thus obtained. The latter is in the form of colorless prisms, nonhygroscopic, insoluble in ether, benzene, toluene and cyclohexane, and soluble in water, methanol and ethanol. It does not contain any impurities such as chloride, acetate, formate, sulfate and the like ions.

It does not lose its water of crystallization by drying at 60° C. to constant weight, but dried at 110° C., it supplies quantitatively pure anhydrous crystalline racemic sodium parahydroxymandelate which has a solubility in water at 20° C. of 19.0 g per 100 g. Such an aqueous solution acidified to pH=1 or treated with cation exchange resin with sulphonic groups, leads to the pure racemic parahydroxymandelic acid.

The invention also relates to the use of the crystalline racemic sodium parahydroxymandelate in the industrial manufacture of crystalline sodium paraformylphenolate.

It is known that the cleavage of mandelic acids gives rise to aromatic aldehydes (U.S. Pat. No. 2,062,205). Moreover in French patent application No. 79 12.173 there is claimed a process for the preparation of crystalline sodium paraformylphenolate from phenol and glyoxylic scid. Now, it has been discovered that crystalline racemic sodium parahydroxymandelate enables crystalline sodium paraformylphenolate to be obtained with excellent yields.

According to the invention, the process consists of subjecting a sodic aqueous solution of crystalline racemic sodium parahydroxymandelate to catalytic decarboxylating oxidizing degradation and then, after removal of the catalyst, of concentrating the solution obtained until the start of crystallization while hot, then draining the cooled suspension and finally drying the precipitate collected to constant weight under vacuum at 20° C. Sodium paraformylphenolate crystallized with two molecules of water is thus isolated. If the precipitate collected is dried to constant weight under vacuum at 100° C., anhydrous crystalline sodium paraformylphenolate is isolated.

More precisely, the process consists of subjecting an aqueous solution containing from 2 to 25% of sodium parahydroxymandelate crystallized with one molecule of water and from 1 to 25% of sodium hydroxide to catalytic decarboxylating oxidizing degradation at a temperature $\leq 140°$ C. and at a pressure of oxygen $\leq 6$ bars in the presence of cupric salts alone or in admixture with other salts of metals of Group VIII of the MENDELEIEV table for 0.1 to 5 hours, of removing the catalyst by filtration, of then concentrating the filtrate hot until the start of crystallization, then draining and washing with a little iced water the precipitate obtained after leaving the suspension for some hours at a temperature close to +5° C. and finally drying to constant weight under vacuum at 20° C., in the presence of potassium hydroxide in pellets, the sodium paraformylphenolate crystallized with two molecules of water, thus obtained.

DESCRIPTION OF PREFERRED EMBODIMENTS

The following examples are given purely by way of non-limiting illustration of the invention.

EXAMPLE 1

A solution of 296 g (2 moles) of 50% glyoxylic acid in water, 564 g (6 moles) of phenol and 160 g (4 moles) of sodium hydroxide in pellets in 3600 g of water is heated for 30 minutes to 82±2° C., with stirring and under a nitrogen atmosphere. Then, after cooling, the reaction solution is brought to pH=6.7±0.2 with acetic acid, then the unconverted phenol is extracted with 1,2-dichloroethane. Thus, after removal of the extraction solvent, 376 g (4 moles) of phenol are isolated. The aqueous solution is then concentrated hot under vacuum to 30% of its weight and then left to crystallize for some hours towards 5±2° C. Finally, the crystalline precipitate formed is drained and washed with ice water and then dried on a fluidized bed at 40° C. to constant weight. 254 g (1.22 mole) of sodium parahydroxymandelate crystallized with one molecule of water is thus obtained in the form of colorless prisms, namely a yield of 61% of the theoretical calculated with respect to the glyoxylic acid used.

Microanalysis: $C_8H_9NaO_5$.

| MW = 208.15 | C % | H % | $H_2O$ %* |
|---|---|---|---|
| calculated | 46.16 | 4.36 | 8.65 |
| found | 46.1 | 4.5 | 8.9 |

*Determined by the method of K. FISCHER.

sulphuric ash 34.0% (theoretical 34.2%)

Search of $Cl^-$ ions by the silver nitrate test: negative.

Search of $SO_4^{--}$ ions by barium chloride test: negative.

Physical Analyses Acidimetry carboxylate function 4.83±0.05 meq/g, namely 100±1% of theory, phenol function 4.77±0.05 meq/g, namely 99.3±1% of theory, infrared (KBr)-spectrum in agreement with the proposed structure.

NMR of the proton at 60 MHz in deuteriated DMSO (internal reference TMS). 3.9 ppm, 3H, m, $H_2O$ and OH benzylic, 4.42 ppm, 1H, s, CH benzylic, 6.8 ppm, 4H, m, aromatic.

The pure racemic parahydroxymandelate crystallized with one molecule of water, dried at 110° C., supplies pure anhydrous crystalline racemic parahydroxymandelate.

This product is in the form of colorless prisms, very soluble in water, methanol and ethanol, insoluble in benzene, ether and toluene.

EXAMPLE 2

Procedure is as in Example 1, but at the end of the reaction, after neutralization of the reaction solution with acetic acid, this solution is concentrated hot at ambient pressure to about one-third of its weight and then the azeotropic distillation of the phenol is continued until the end of the entrainment keeping the volume constant in the boiler by the addition either of water, or of steam. After complete removal of the unconverted phenol, the reaction medium is left to crystallize for some hours towards 5±2° C., then the crystalline precipitate obtained is drained and washed with ice water and finally it is dried on a fluidized bed at 40° C. to constant weight. 254.3 g (1.22 mole) of pure racemic sodium parahydroxymandelate crystallized with one molecule of water is thus obtained in the form of colorless prisms, namely a yield of 61% of the theoretical calculated from the glyoxylic acid utilized.

EXAMPLE 3

104 g (0.5 mole) of racemic sodium parahydroxymandelate crystallized with one molecule of water, 1 g of cupric sulphate pentahydrate, 1 g of cobalt (II) acetate tetrahydrate in 1350 g of a 6.8% by weight aqueous solution of sodium hydroxide is heated for four hours at 120° C. in an autoclave in an oxygen atmosphere at a pressure of 4 bars. After cooling, the catalyst is filtered off, then the filtrate is concentrated hot under vacuum to one-third of its weight, it is then left to crystallize towards 5±2° C. for some hours. Finally, the crystalline precipitate obtained is drained and washed with ice water. It is dried under vacuum at 20° C. to constant weight in the presence of pelletized potassium hydroxide. 77.5 g (0.43 mole) of sodium paraformylphenolate crystallized with 2 molecules of water in the form of colorless platelets having a melting point of 122±3° C. with decomposition (literature M.P.=122±3° C., French Patent Application No. 79 12.173) is thus isolated, namely a yield of 86% of the theoretical calculated from the sodium parahydroxymandelate crystallized with one molecule of water utilized. If the drying is carried out at 100° C. under vacuum to constant weight, anhydrous crystalline sodium paraformylphenolate is obtained with the same yield.

It is self-evident that the present invention has only been described purely by way of non-limiting illustration and that any modification could be introduced therein without departing from its scope as defined in the appended claims.

We claim:

1. Pure crystalline racemic sodium parahydroxymandelate free from any ions of chloride, acetate, formate and sulfate group.

2. Pure crystalline racemic sodium parahydroxymandelate according to claim 1, crystallized with one molecule of water.

3. Pure anhydrous crystalline sodium parahydroxymandelate according to claim 1.

4. Pure crystalline racemic sodium parahydroxymandelate according to claim 1 having a solubility in water at 20° C. of 19 g per 100 g.

* * * * *